United States Patent [19]
Senba et al.

[11] Patent Number: 5,599,661
[45] Date of Patent: Feb. 4, 1997

[54] REAGENT FOR MEASURING DIRECT BILIRUBIN

[75] Inventors: Shoji Senba; Keisuke Kurosaka; Hitoshi Kondo, all of Kyoto; Masami Kojima; Hiroshi Suzuki, both of Chiba-ken, all of Japan

[73] Assignees: Unitika, Ltd., Hyogo; Iatron Laboratories, Inc., Tokyo, both of Japan

[21] Appl. No.: 365,158

[22] Filed: Dec. 28, 1994

[30] Foreign Application Priority Data

Dec. 28, 1993 [JP] Japan .................................. 5-338661
Oct. 27, 1994 [JP] Japan .................................. 6-264197

[51] Int. Cl.$^6$ ........................... C12Q 1/00; C12Q 1/26; G01N 33/48; G01N 33/20

[52] U.S. Cl. ........................... 435/4; 435/25; 435/28; 436/63; 436/97; 436/74

[58] Field of Search ............................ 435/4, 25, 28; 436/97, 63, 74

[56] References Cited

U.S. PATENT DOCUMENTS

| | | | |
|---|---|---|---|
| 3,652,222 | 3/1972 | Denney et al. | 436/97 |
| 4,600,689 | 7/1986 | Matsui et al. | 435/25 |
| 4,788,153 | 11/1988 | Detwiler et al. | 436/97 |
| 4,892,833 | 1/1990 | Weiss et al. | 436/97 |
| 5,112,769 | 5/1992 | Modrovich | 436/97 |
| 5,149,272 | 9/1992 | Wu et al. | 436/97 |
| 5,262,304 | 11/1993 | Taniguchi | 436/97 |
| 5,278,073 | 1/1994 | Grandjean | 436/97 |

*Primary Examiner*—John Kight
*Assistant Examiner*—Louise N. Leary
*Attorney, Agent, or Firm*—Wenderoth, Lind & Ponack

[57] ABSTRACT

A reagent system and method are described for optically measuring direct bilirubin by the reaction of a bilirubin oxidase, oxidizing agent or diazonium salt, with the direct bilirubin, wherein a tetrapyrrole compound is provided in the presence of the bilirubin oxidase, oxidizing agent or diazonium salt. It is possible to accurately measure the direct bilirubin, which is known to increase considerably in the biological fluids of patients having obstructive jaundice, etc. The reagent system and method are useful in clinical settings, etc.

9 Claims, 9 Drawing Sheets

REAGENT FOR MEASURING DIRECT BILIRUBIN

FIELD OF THE INVENTION

The present invention relates to reagents to measure direct bilirubin present in biological fluids.

PRIOR ART

Bilirubin is a yellow pigment belonging to tetrapyrroles. It is a degradative product of heme, and is known to be present in the bile in large quantities. Bilirubin in the biological fluids is mainly composed of direct and indirect bilirubin.

The indirect bilirubin increases significantly in hemolytic anemina and jaundice, etc. while the direct bilirubin increases in obstructive jaundice, etc. For this reason, fractional determination is important in clinical diagnosis, etc. Total and direct bilirubin have conventionally been measured in clinical laboratories. The correct determination of direct bilirubin is indispensable in clinical laboratories.

Various methods are available for determining the direct bilirubin, including a method to use diazo reagents, a method to use high performance liquid chromatography (HPLC), a method to use oxidase such as bilirubin oxidase, a method to use oxidizing agents such as vanadic acid ions or manganic ions, etc.

Various methods have been reported using diazo reagents based on the different kinds of diazotizing accelerator or the different determination method for the produced azobilirubin. They include, for example, the reagent reported by Malloy & Evelyn [Journal of Biological Chemistry, Vol. 119, p481 (1937)].

Differential determination methods by HPLC include, for example, method-using the phosphate buffers and isopropanol as a eluent in a reversed-phase HPLC column reported by Lauff et al [Journal of Chromatography, Vol. 226, p391 (1981)].

In the methods using oxidases, bilirubin is oxidized by oxidases, with disappearance of its yellow color at around 450 nm. The change in absorbance is then measured before and after reaction to measure bilirubin. It is possible to specifically oxidize only the direct bilirubin by varying reaction conditions. The reagents used in these methods include, for example, reagents using bilirubin oxidase [Clinical Chemistry, Vol. 20, p783 (1974)] and reagents using laccase, tyrosinase, ascorbate oxidase and other oxidases (Japanese patent 62-33880). Further, reagents for measuring direct bilirubin with bilirubin oxidases so that they react with only the direct bilirubin by suitably selecting pH, buffers, and surfactants, have been proposed.

These reagents for measuring direct bilirubin include, for example, reagents to determine the direct bilirubin by allowing bilirubin oxidases to react in buffers of pH 9 to 11 (Japanese patent 5-68240), reagents to determine the direct bilirubin by allowing bilirubin oxidases to react in acid buffers of pH 5 to 6 containing anionic surfactants (Japanese patent 5-9066), reagents to determine the direct bilirubin by allowing bilirubin oxidases to react in buffers of pH 3.5 to 4.5 (Japanese patent 61-44000), reagents to determine the direct bilirubin by allowing bilirubin oxidases to react in buffers of pH 2.0 to 3.3 containing potassium ferrocyanide and/or potassium ferricyanide (Japanese application patent 1-5499).

In the methods using oxidizing agents, bilirubin is oxidized by oxidizing agents, with disappearance of its yellow color at around 450 nm, and the change in absorbance is measured before and after the reaction to measure bilirubin. It is also possible to specifically oxidize only the direct bilirubin by varying reaction conditions. The reagents used in these methods include, for example, reagents using vanadic acid ions [Clinical Chemistry, Vol. 22, p116 (1993)]. Further, reagents for measuring direct bilirubin, in which oxidizing agents react only with the direct bilirubin by suitably selecting reaction retarders, buffers, etc. for the indirect bilirubin, have been proposed. These reagents for measuring direct bilirubin include, for example, a reagent to determine the direct bilirubin by using vanadic acid ions or manganic ions as oxidizing agent, and by using one or more compounds from the group of hydrazines, hydroxylamines, oximes, aliphatic polyvalent amines, phenols, water-soluble macromolecules and nonionic surfactant with HLB value 15 or above as the reaction retarder for the indirect bilirubin (Japanese patent application 5-18978).

The conventional methods to differentially determine the direct bilirubin by using the HPLC have sufficiently separated to the other bilirubin species but they use expensive and special equipment, take a long time to analyze, can not analyze a number of specimens at a time, or otherwise have a number of problems.

On the other hand, the methods to determine the direct bilirubin by allowing bilirubin oxidases or other oxidases to react have the merits of optical measurements, are simple to use and have a relatively high precision. Because they do not have sufficient ability for separation of bilirubins the reaction with direct bilirubin is not perfect or they react with not only the direct but also a part of the indirect bilirubin. In addition, these reactions must be carried out outside the optimum pH range for bilirubin oxidases. For these reasons, a large amount of enzymes must be used and the costs of reagents must be expensive. To solve the problem, the inventors of the present invention improved specificity for the direct bilirubin by adding fluorides and/or reducing agents and proposed reagents for measuring direct bilirubin that can be used in the optimum pH range of BOD (Japanese patent application 5-276992). It should be noted, however, that the ability for separation of this reagent is not perfect.

Reagents using vanadic acid ions or manganic ions as oxidizing agents will react with not only the direct but also a part of the indirect bilirubin, resulting in insufficient fractional determination even when the retarders for the indirect bilirubin such as hydrazines, hydroxylamines, oximes, etc. are used.

The methods using diazo reagents are designed for fractionation of direct and indirect bilirubin, in which diazotizing reaction accelerators are contained or not. The problem with this type of method is imperfect separation just like the methods using oxidases or oxidizing agents. The imperfection is particularly conspicuous when measuring specimens of low albumin content and specimens containing salicylic acids and other medicines.

SUMMARY OF THE INVENTION

The inventors of the present invention studied means to solve the problems in the conventional reagents for measuring direct bilirubin in consideration of the above-mentioned circumstances. As a result, they completed the present invention by finding that in the specimens the direct bilirubin can be measured with good precision without reaction of the indirect bilirubin by allowing tetrapyrrole compounds to exist in the reagents for measuring direct bilirubin that specifically oxidize only the direct bilirubin bin by bilirubin oxidases; in the reagents for measuring direct bilirubin that specifically oxidize only the direct bilirubin by oxidizing agents; and in the reagents for measuring direct bilirubin that convert the direct bilirubin into azobilirubin by the reaction of diazonium salts.

More specifically, the present invention provides reagents for measuring direct bilirubin which optically measure the absorbance change in the direct bilirubin by the reaction of bilirubin oxidase, wherein tetrapyrrole compounds are allowed to exist with the bilirubin oxidase.

Further, the present invention provides reagents for measuring direct bilirubin which optically measure the absorbance change in the direct bilirubin by the reaction of an oxidizing agent, wherein tetrapyrrole compounds are allowed to exist with the oxidizing agents.

Still further, the present invention provides reagents for measuring direct bilirubin which optically measure the absorbance change in the direct bilirubin by the reaction of diazonium salts, wherein tetrapyrrole compounds are allowed to exist with the diazonium salts.

DETAILED DESCRIPTION OF THE INVENTION

The reagent for measuring direct bilirubin according to the present invention may be a two-part reagent system comprising a first reagent containing buffer; tetrapyrrole, and a second reagent to be mixed with the first reagent when in use, or a single reagent system in which all components are contained in one solution. In the measuring reagent the second reagent in the two-component reagent system is selected from a reagent containing bilirubin oxidases, a reagent containing oxidizing agents and a reagent containing diazonium salts.

The kinds of tetrapyrrole compounds are not particularly limited in the present invention. For example, bilirubin, biliverdin, urobilinogen, etc. may be used independently or in combination. The use of bilirubin is preferable. The concentration is 0.01 to 100 ug/ml, preferably 0.1 to 40 ug/ml. If the concentration of the tetrapyrrole compounds is below the lower limit of the above range, the indirect bilirubin is partially oxidized together with the direct bilirubin, which is not preferable. Bilirubin oxidases used in the measuring reagent of the present invention may be, for example, enzymes derived from Myrothecium or Trachyderma. The amount required is 0.001 to 200 units/ml, preferably 0.005 to 20 units/ml.

The buffer to be used should have buffering capacity for pH 6.5 or less, preferably between pH 3.0 to 6.5, which is favorable for the enzymes to be used from the viewpoint of their stability and activity. Examples include phthalic acid-sodium hydroxide buffer, malic acid-sodium hydroxide buffer, citric acid-sodium citrate buffer, etc. The concentration of the buffer is 20 to 500 mM, preferably 30 to 300 mM.

Other components may be added such as p-toluenesulfonic acids, benzoic acids and other aromatic carboxylic acids, surfactants, alanines, serines and other amino acids, mannitol and other sugars, polyethylene glycol and other polyols, NaCl and other salts, albumin and other proteins, etc.

The kinds of vanadic acid ions used as oxidizing agent in the measuring reagent of the present invention are not particularly limited. Favorable examples include those containing $VO_3^-$, $VO_4^{3-}$ or other pentavalent vanadium. Although acids may be used, it is preferable to use vanadic acids in the form of salts such as lithium, sodium, potassium or other alkaline metals or ammonium from the viewpoint of solubility, etc.

Manganic ions to be used as oxidizing agent in the measuring reagent of the present invention may be not only ordinary manganic salts such as manganese (III) acetate but also those compounds chelated with acetylacetone, ethylenediaminetetraacetic acid or other chelating agents.

The concentration of vanadic acid ions and manganese ions is not particularly limited provided that it is sufficient to allow oxidation of bilirubin contained in the specimen. It is generally 0.1 to 50 μg ions/ml, preferably 0.5 to 10 μg ions/ml.

The reaction retarding agent for the indirect bilirubin to be used in the measuring reagent of the present invention may be hydrazines, hydroxylamines, oximes, aliphatic polyvalent amines, phenols, water soluble macromolecules, nonionic surfactant of HLB value 15 or above, etc. The kinds of these reaction retarding agents are not particularly limited provided that the measurement of the direct bilirubin is not affected. Preferable examples for each type is shown below. Hydrazine species include, for example, hydrazines, phenylhydrazines and their mineral acid salts (hydrochloric acid salts, sulfate, etc.). Hydroxylamine species include, for example, hydroxylamines, phenylhydroxylamines and their mineral acid salts (hydrochloric acid salts, sulfate, etc.). Oxime species include, for example, acetoxime, diacetylmonooxime, salicylaldoxime, etc. Aliphatic polyvalent amine species include, for example, tetraethylenepentamine hexamethylenetetramine, triethylenetetramine, etc. Phenol species include, for example, phenol, p-chlorphenol, p-acetamidephenol, 4-chlor-1-naphthol, β-naphthol, etc. Water soluble macromolecules include, for example, polyvinylalcohol, polyvinylpyrrolidone, etc. Nonionic surfactants of HLB value 15 or above include, for example, Emulgen-123p (polyoxyethylenelaurylether, Kao brand name). Emulgen-950 (polyoxyethylenenonylphenylether, Kao brand name), Emulgen-985 (polyoxyethylenenonylphenylether Kao brand name), Triton X-405 (polyoxyethyleneisooctylphenylether, Rohm and Haas Co. brand name), etc. These reaction retarding agents are effective for retarding oxidation of the indirect bilirubin independently. The effect may be enhanced when two or more reaction retarding agents are used in combination. These reaction retarding agents are adequately selected for each application. Concentration of these reaction retarding agents is not particularly limited provided that they can retard oxidation of the indirect bilirubin in the specimen. It may depend on the kinds of retarding agents to be used, but is generally in the 0.01 to 10% (W/V) range.

When chelating agents are allowed to coexist in the measuring reagent of the present invention, the reagent blank value decreases to improve precision of analysis; the reagent is stabilized; and oxidation of bilirubin is accelerated. Favorable chelating agents that are used for the above purpose include, for example, ethylenediaminetetraacetic acid (EDTA), nitrotriacetic acid (NTA), cyclohexanediamine-tetra-acetic acid (CyDTA), diethylene-triamine-penta-acetic acid (DTPA), hydroxyethyl ethylenediaminetriacetic acid (EDTA-OH), tri-ethylenetetraimine-hexa-acetic acid (TTHA), hydroxy-ethyliminc-di-acetic acid (HIDA), 1-hydroxyethane-1, 1-diphosphoric acid or their alkaline metal salts (for example, lithium salts, sodium salts, potassium salts, etc.) and ammonia salts, etc. Concentration of these chelating agents is not particularly limited provided that the measurement of bilirubin is not affected. It is generally 0.02 to 65 mM, preferably 1 to 40 mM, more preferably 1 to 25 mM.

Diazo reagents used in the measuring reagent of the present invention may be any known diazo reagent used in the conventional methods, such as, for example, unstabilized diazo reagents disclosed in the Japanese application patent 56-12555 (diazotized derivatives of sulfanilic acid, o-dianisidine, p-chloroaniline, 1,5-dichloroaniline, 2,4-dichloroaniline, 2-methoxy-4-nitroaniline, 1-aminoanthraquinone, 2-nitroaniline, and 4-chloromethylaniline) and stabilized diazo reagents (borate tetrafluoride, 1,5-naphthalenedisulfonic acid salts and zinc chloride salts of the above-mentioned unstabilized diazo reagents). In particular, 2,4-dichlorphenyl diazonium-1,5-naphthalenedisulfonic acid and its salts (for example, sodium salts, potassium salts, etc.), p-sulfanylbenzene diazonium-1,5-naphthalenesulfonic acid and tis salts, p-nitrobenzene diazonium-tetra fluoride boric acid and its salts, diazosulfanyl acid-tetra-fluoride boric acid and its salts, and other stabilized diazonium salts allow simple measurement and thus are effective diazo reagents to be used in the measuring reagent of the present invention.

Other reagents used in the measuring reagent of the present invention, such as buffers and antiseptics, may be appropriately selected from buffers used in the known chemical oxidation methods, bilirubin oxidase methods, etc. (for example, phosphate, citrate, succinate, acetate, phthalate etc.) and from antiseptics such as paraben. Their concentration and the pH value of the measuring reagents may also be appropriately set according to those specified for reagents in said known methods.

The present invention also allows preparation of the reagents for measuring direct bilirubin by appropriately selecting the above-mentioned constituents and mixing them according to known methods. A favorable example comprises a first reagent containing 10 to 200 mM phthalate buffer adjusted to pH 4.7 to 6.5, 0.005 to 0.5% polyethyleneglycolmono-p-isooctylphenylether, 5 to 100 mM alanine, 1 to 100 mM p-toluenesulfonic acid, 0.001 to 1% human serum albumin, 0.05 to 200 mM sodium fluoride, 0.02 to 10 mM N-acetylcysteine, and 0.1 to 10 µg/ml bilirubin, and a second reagent containing 0.001 to 100 units/ml bilirubin oxidase and 10 to 200 mM phthalate buffer adjusted to pH 4.7 to 6.5. It is possible to prepare more accurate reagent for measuring g direct bilirubin by adding 1 to 10 µg/l bilirubin to a first reagent comprising commercially available diagnostical reagents for measuring direct bilirubin, for example reagents NESCAUTO D-BIL-VE (Nippon Shoji Kaisha Ltd.), Ekdia DB (EIKEN Chemical), or D-BIL reagent C "Kokusai" (International Reagents Corp.), etc.

The direct bilirubin can be measured in the method below, for example, using the reagents of the present invention derived in the above procedures.

First, for the reagent for measuring direct bilirubin using bilirubin oxidase, the first reagent may comprise, for example, a buffer and bilirubin or other tetrapyrrole compounds to which an adequate amount of various specimens containing bilirubin (blood plasma, serum, urine or other biological fluids) is added to make a solution. The solution is pre-heated in the cell of a spectrophotometer and absorbance is measured at a specified wavelength for the solution (460 nm or thereabout) (absorbance 1). A second reagent containing bilirubin oxidase is added to the solution; reaction is allowed to take place for 1 to 10 minutes for the direct-type bilirubin to be oxidized. The absorbance is measured again at 460 nm or thereabout (absorbance 2). Change in absorbance (A) at the above-mentioned specified wavelength is determined by multiplying absorbance 1 and 2 by a dilution factor of the reagent. Then, a standard substance containing the direct-type bilirubin of a known concentration is measured in the same procedures to derive the change in absorbance (B), and to prepare the calibration curves. Change in absorbance (A) is then overlaid on the calibration curve to determine the amount of the direct bilirubin present in the specimen. Using the change in absorbance (A) and (B), the direct bilirubin content of the specimen is calculated in the equation below.

Concentration of direct bilirubin in specimen (mg/dl)=A/B×concentration of direct bilirubin in standard solution (mg/dl)

Volume of a specimen is preferably 0.005 to 0.1 ml. The specified wavelength is not limited to 460 nm but may be any wavelength in the 400 to 480 nm range. The volume of the first and the second reagent and the specimen may be varied appropriately.

The reaction takes place under normal conditions. Reaction temperature, for example, is 25 to 45 degC., preferably 35 to 40 degC., and reaction time 1 to 30 minutes, preferably 3 to 15 minutes.

Measurement can be taken in the same manner for the measuring reagent using an oxidizing agent. More specifically, the first reagent comprises a buffer, reaction retarding agent and, when required, chelating agents, etc., to which a specimen containing bilirubin is added to make a solution. Absorbance of the solution is measured at a specified wavelength (between 430 and 460 nm) (absorbance 1). A second reagent comprising vanadic acid ions or manganic ions and, when required, chelating agents, is added to the above solution. Oxidation of bilirubin is allowed to occur at 25 to 40 degC. for 3 to 15 minutes. Absorbance at the specified wavelength is measured again (absorbance 2). Change in absorbance (A) at the above-mentioned specified wavelength is determined by multiplying absorbance 1 and 2 by a dilution factor of the reagent. Then, the change in absorbance (A) is overlaid on the calibration curve derived from the change in absorbance (B) obtained by allowing a standard substance to react, to measure the amount of the direct bilirubin in the specimen. Alternatively, the above equation is used to calculate the amount of the direct bilirubin in the specimen.

The same procedures apply to the measuring reagent using a diazonium salt. A buffer is used as the first reagent; a specimen containing bilirubin is added to the buffer to make a solution; and absorbance of the solution is measured at a specified wavelength (between 540 and 600 nm) (absorbance 1). Then, the second reagent containing diazonium salts is added to the above solution and reaction is allowed to occur at 25 to 40 degC. for 3 to 15 minutes. The absorbance of the specified wavelength is measured again (absorbance 2). Change in absorbance (A) is determined from absorbance (1) and (2), and the amount of the direct bilirubin in the specimen is measured from the change in absorbance (B) which is measured beforehand. An alternative method of the use of the measuring reagent with diazonium salts is described below. The first reagent containing diazonium salts is mixed with a specimen containing bilirubin. The mixture is allowed to react at 25 to 40 degC. for 3 to 15 minutes. A buffer is added to the solution. The solution is further allowed to react at 25 to 40 degC. for 3 to 15 minutes. The absorbance absorbance of this solution is measured at a specified wavelength (between 540 and 660 nm). Then, the absorbance is overlaid on the calibration curve derived from the absorbance obtained by allowing a standard substance to react, to measure the amount of the direct bilirubin in the specimen.

Other measuring methods are also available. For example, in the above method using the measuring reagent containing an oxidizing agent, the absorbance of the solution comprising a mixture of the first reagent and the specimen is taken as absorbance 1 and the absorbance of a solution comprising a pre-mix of the first and the second reagent which is allowed to react with the specimen is taken as absorbance 2. Using these two measured values, the concentration of the direct bilirubin in the specimen is measured by following the above procedures.

As described above, the reagents of the present invention do not react with the indirect bilirubin contained in a bilirubin-containing specimen because the reagents of the present invention allow tetrapyrrole compounds to exist with bilirubin oxidases, vanadic acids or manganic ions, or diazo reagents. It is thus possible to measure the direct bilirubin with good precision.

EXAMPLE

The present invention is illustrated by the following examples which, however, are not to be construed as limiting the invention to their details. Absorbance was measured in the examples using a Hitachi 7070 automatic analyzer.

Preparation of Specimen

Specimen 1:

We prepared indirect bilirubin specimens of 0, 0.2, 0.4, 0.6, 0.8 and 1.0 mg/dl bilirubin solutions containing bovine serum albumin using a bilirubin solution comprising bilirubin (sigma) dissolved in 100 mM tris-hydrochloric acid buffer (pH 8.0). The concentrations of direct bilirubin of these specimens were 0 mg/dl. The concentration of bovine serum albumin (Boehringer Mannheim Japan) solution in a 100 mM tris-hydrochloric acid buffer (pH 8.5) was 3.2 g/dl.

Specimen 2:

Using the above bovine serum albumin solution and Ortho liquid normal control serum (Ortho Diagnostics Corp. brand name, hereafter abbreviated Ortho normal), we prepared a specimen of Ortho normal not containing bilirubin.

Specimen 3:

A specimen containing 0.5 mg/dl bilirubin was prepared by using the above bilirubin solution and Ortho normal.

Specimen 4:

A specimen containing 1.0 mg/dl bilirubin was prepared by using the above bilirubin solution and Ortho normal.

Specimen 5:

A direct bilirubin specimen was prepared by diluting High Level Check BIL (Takara Shuzo Co., Ltd. brand name) solution with physiological saline.

Preparation of Reagents

Reagent 1:

Reagent 1 was prepared by containing 60 mM (pH 5.0), 0.01% polyethyleneglycolmono-p-isooctylphenylether, 0.002% human serum albumin, 40 mM p-toluenesulfonic acid, 2.0 mM N-acetylcysteine, 2.0 mM sodium fluoride, 40 mM alanine, and 0.5 µg/ml bilirubin.

Reagent 2:

Reagent 2 was prepared by adding 5.0 units/ml bilirubin oxidase derived from Trachyderma (Takara Shuzo Co., Ltd. to reagent 1.

Reagent 3:

Reagent 3 was prepared by adding 5 µg/ml bilirubin to the first reagent of commercially available diagnostic reagent kit, reagent for measuring direct bilirubin NESCAUTO D-BIL-VE (Nippon Shoji Kaisha Ltd.).

Reagent 4:

The second reagent of NESCAUTO D-BIL-VE (Nippon Shoji Kaisha Ltd.).

Reagent 5:

Reagent 5 was prepared by adding 5 µg/ml bilirubin to the first reagent of Sodium Metavanadate DB (Sodium Metavanadate).

Reagent 6:

The second reagent of Sodium Metavanadate DB (Sodium Metavanadate).

Reagent 7:

Reagent 7 was prepared by adding 5 µg/ml bilirubin to the first reagent of D-BIL reagent C "Kokusai" (International Reagents Corp.).

Reagent 8:

The second reagent of D-BIL reagent C "Kokusai" (International Reagents Corp.). [Reagents 4, 6 and 8 contain bilirubin oxidases (Sodium Metavanadate) derived from Myrothecium Amano Pharmaceutical Co., Ltd.]

Reagent 9:

Bilirubin was removed from reagent 1.

Reagent 10:

Bilirubin was removed from reagent 3.

Reagent 11:

Bilirubin was removed from reagent 5.

Reagent 12:

Bilirubin was removed from reagent 7.

Reagent 13:

20 mM hydrochloric acid hydroxylamine and 10 mM hydroxyethanedisulfonic acid were added to 100 mM tartaric acid buffer adjusted to pH 2.9.

Reagent 14:

0.4 ug/ml bilirubin was added to reagent 13.

Reagent 15:

4 ug/ml bilirubin was added to reagent 13.

Reagent 16:

20 ug/ml bilirubin was added to reagent 13.

Reagent 17:

40 ug/ml bilirubin was added to reagent 13.

Reagent 18:

8 mM hydroxyethanedisulfonic acid and 4 mM Sodium Metavanadate were added to a phosphate buffer adjusted to pH 7.0.

Reagent 19:

65 mM hydrochloric acid of pH 1.0.

Reagent 20:

0.4 ug/ml bilirubin was added to reagent 19.

Reagent 21:

4 ug/ml bilirubin was added to reagent 19.

Reagent 22:

20 ug/ml bilirubin was added to reagent 19.

Reagent 23:

40 ug/ml bilirubin was added to reagent 19.

Reagent 24:

A reagent comprising 8.1 mM sulfanilic acid and 1.4 mM sodium nitrite was prepared.

Reagent 25:

A reagent comprising 5.1 mM sulfanilic acid and 0.5 mM sodium nitrite, (developing blue color under the alkaline condition) was prepared.

Reagent 26:

0.4 ug/ml bilirubin was added to reagent 25.

Reagent 27:

4 ug/ml bilirubin was added to reagent 25.

Reagent 28:

20 ug/ml bilirubin was added to reagent 25.

Reagent 29:

40 ug/ml bilirubin was added to reagent 25.

Reagent 30:

22 mM tartaric acid buffer adjusted to pH 13.5.

Example 1

Figure 1:
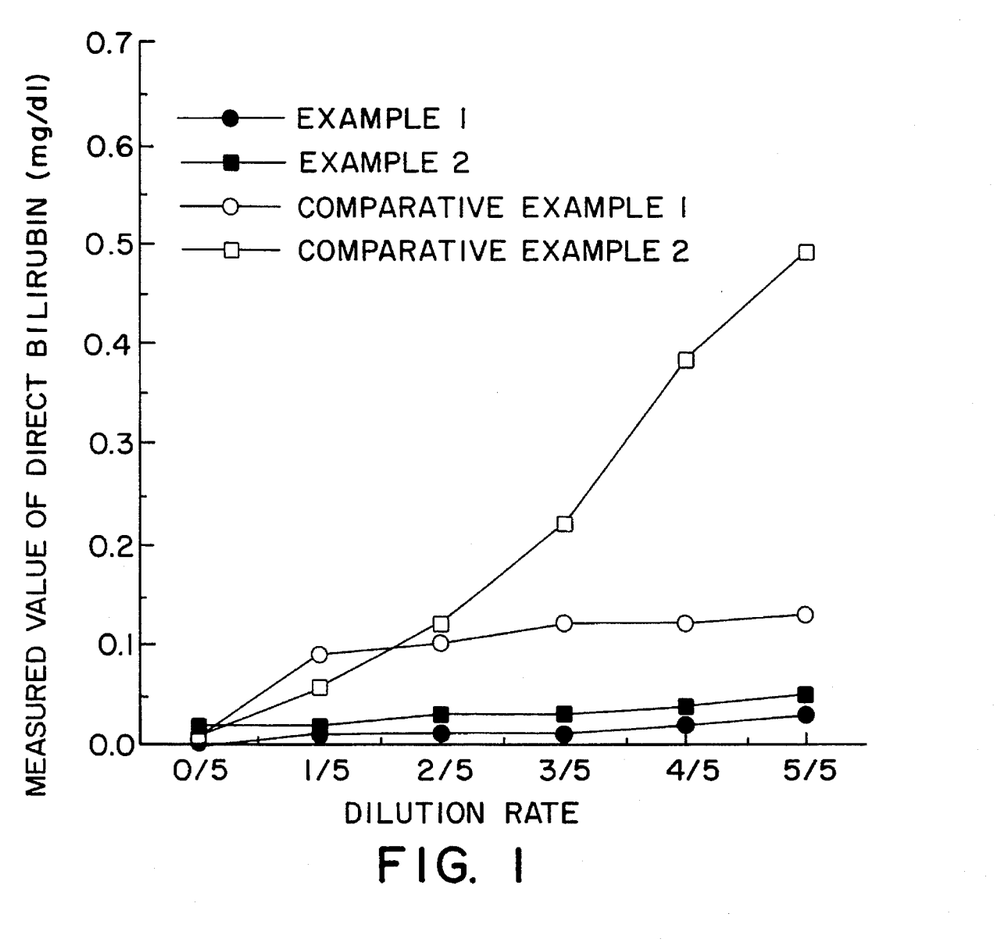
FIG. 1 shows the relation between the measured value of direct bilirubin and the dilution rate of samples wherein the samples are the indirect bilirubin by the reagent of the present invention using enzymes derived from Trachyderma (example 1 and comparative example 1) or Myrothecium (example 2 and comparative example 2) as bilirubin oxidase. Comparative examples are also shown in the figure.

Specimen 1 (0.014 ml) was added to the above reagent 1 (0.28 ml). The mixture was heated at 37 degC for 5 minutes. Sample blanks were corrected for the final volume by assuming the addition of reagent 2 measured at 450 nm. Reagent 2 (0.07 ml) was added and the solution was allowed to react at 37 degC for 5 minutes. Absorbance at 450 nm was measured and the amount of the direct bilirubin in the specimen was determined using ditaurobilirubin of know concentration as the standard. The result is shown in FIG. 1.

Comparative Example 1

The same measurement as in example 1 was taken except that reagent 9 was used in place of reagent 1. The result is shown in FIG. 1 together with that for example 1.

Example 2 to 4

Comparative Example 2 to 4

Figure 2:
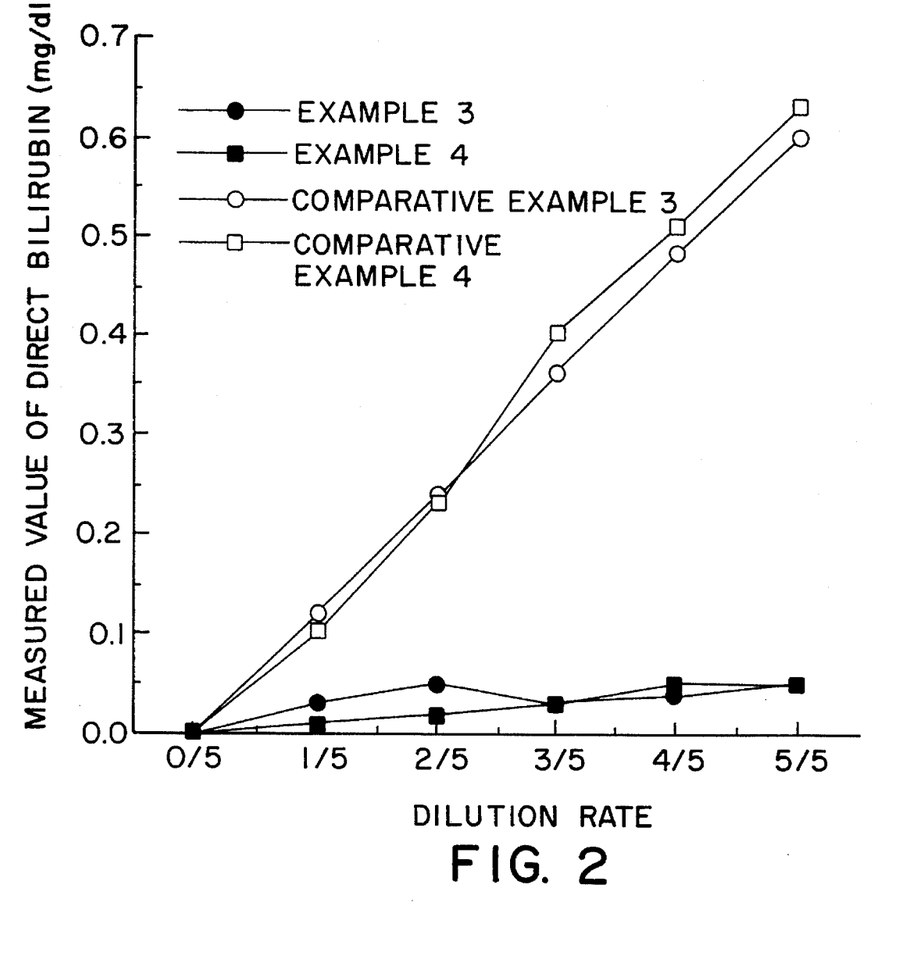
FIG. 2 shows the relation between the measured value of direct bilirubin and the dilution rate of samples wherein the samples are the indirect bilirubin by the reagent (example 3 and 4) of the present invention using enzymes derived from Myrothecium as bilirubin oxidase. Comparative examples are also shown in the figure.
Figure 3:
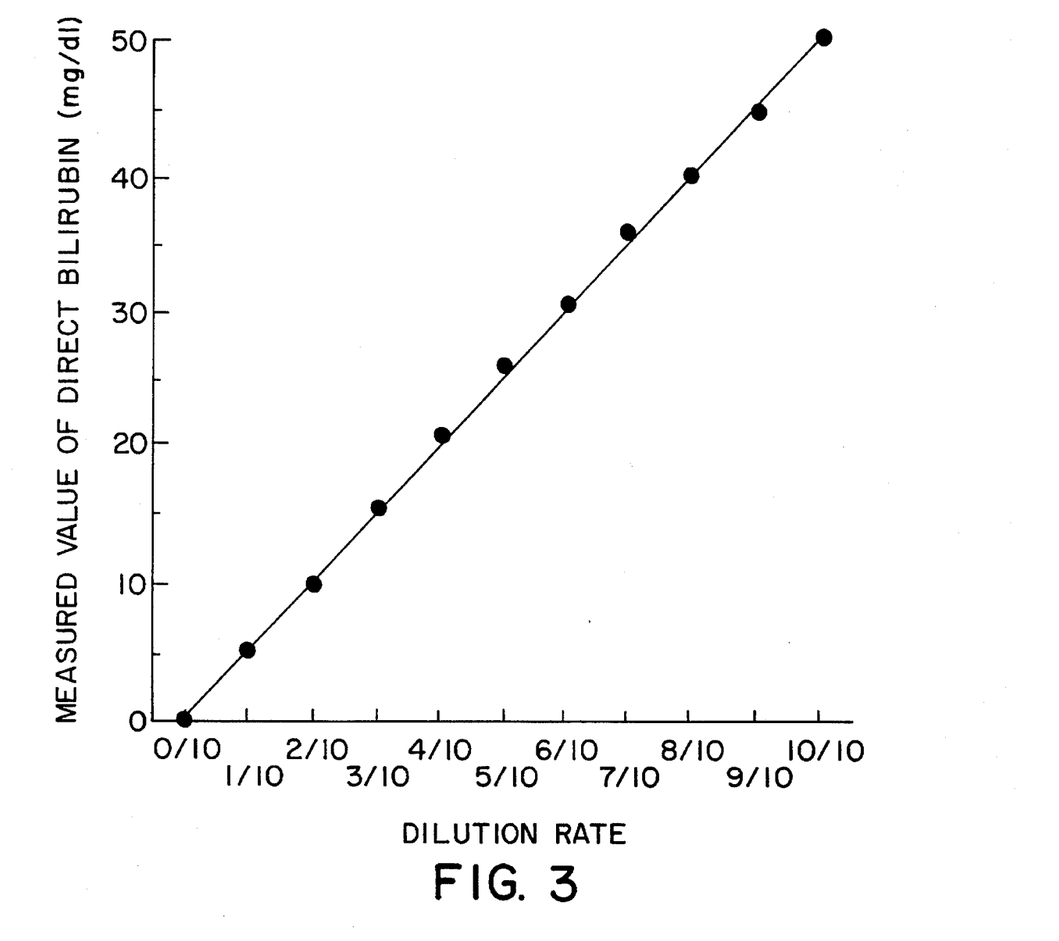
FIG. 3 shows the relation between the measured value of direct bilirubin and the dilution rate of samples wherein the samples are the direct bilirubin by the reagent of the present invention using enzymes derived from Trachyderma as bilirubin oxidase.
Figure 4:
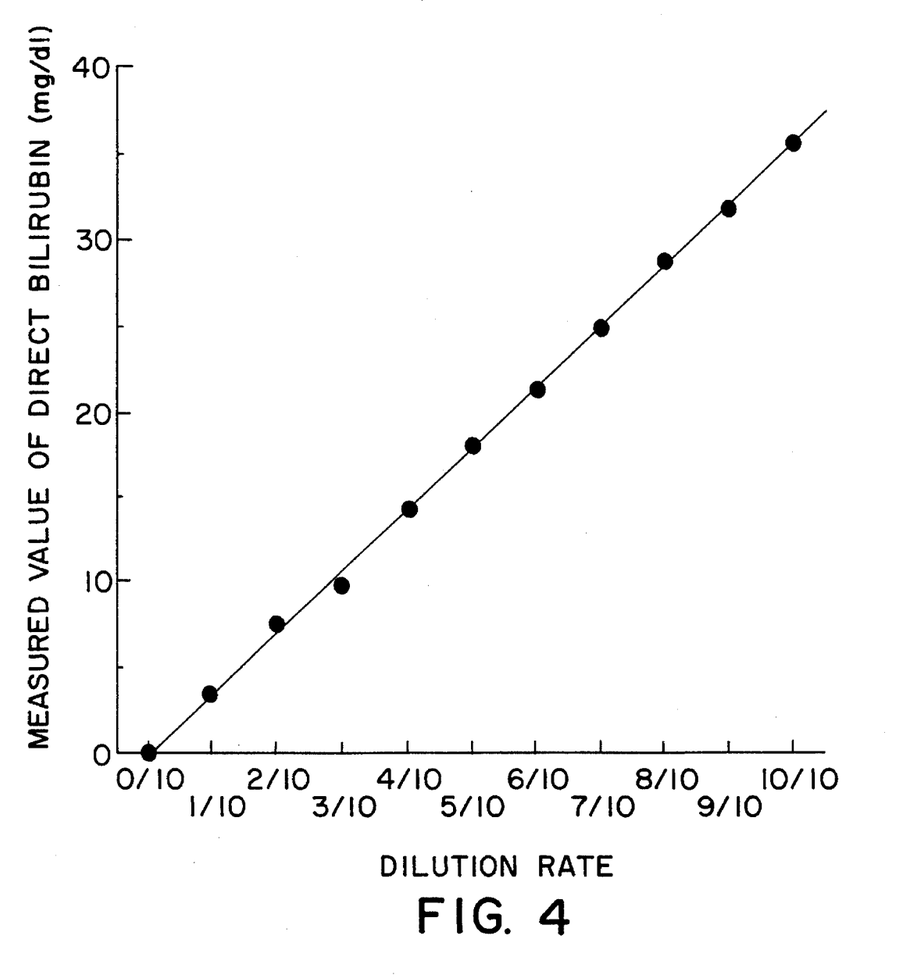
FIG. 4 shows the relation between the measured value of direct bilirubin and the dilution rate of samples wherein the samples are the direct bilirubin by the reagent of the present invention using enzymes derived from Myrothecium as bilirubin oxidase.
Figure 5:
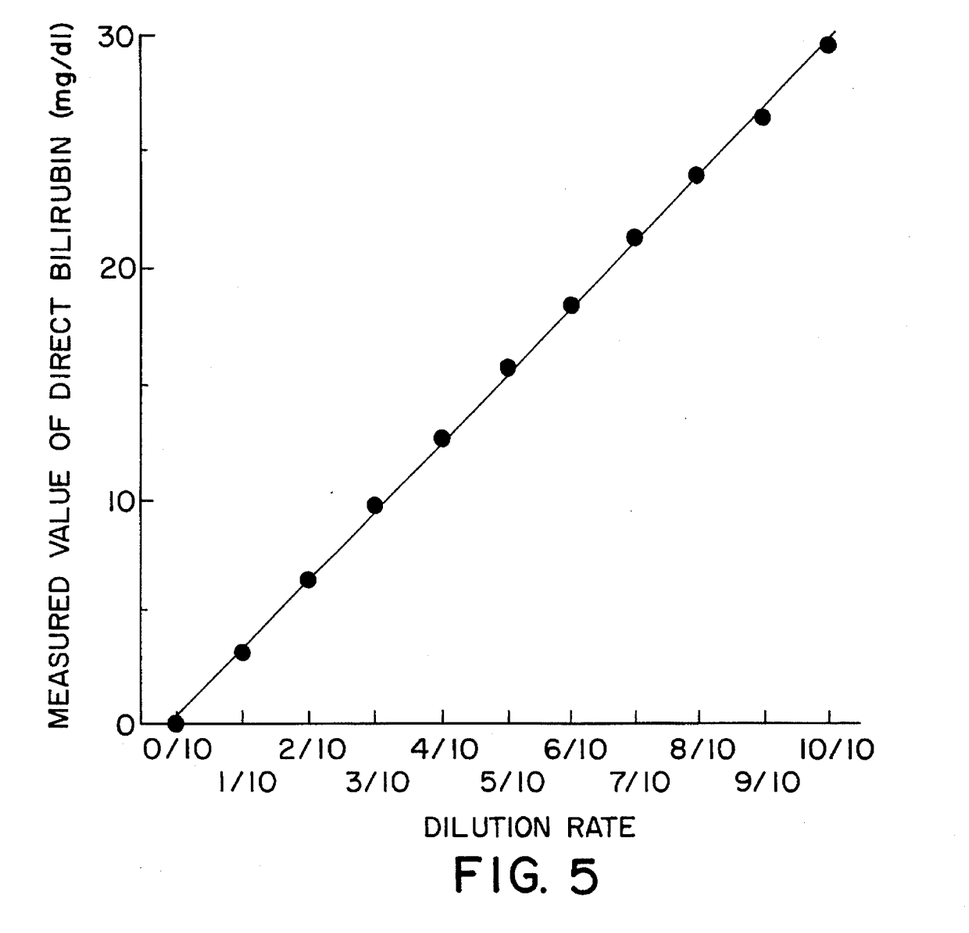
FIG. 5 shows the relation between the measured value of direct bilirubin and the dilution rate of samples wherein the samples are the direct bilirubin by the reagent of the present invention using enzymes derived from Myrothecium as bilirubin oxidase.
Figure 6:
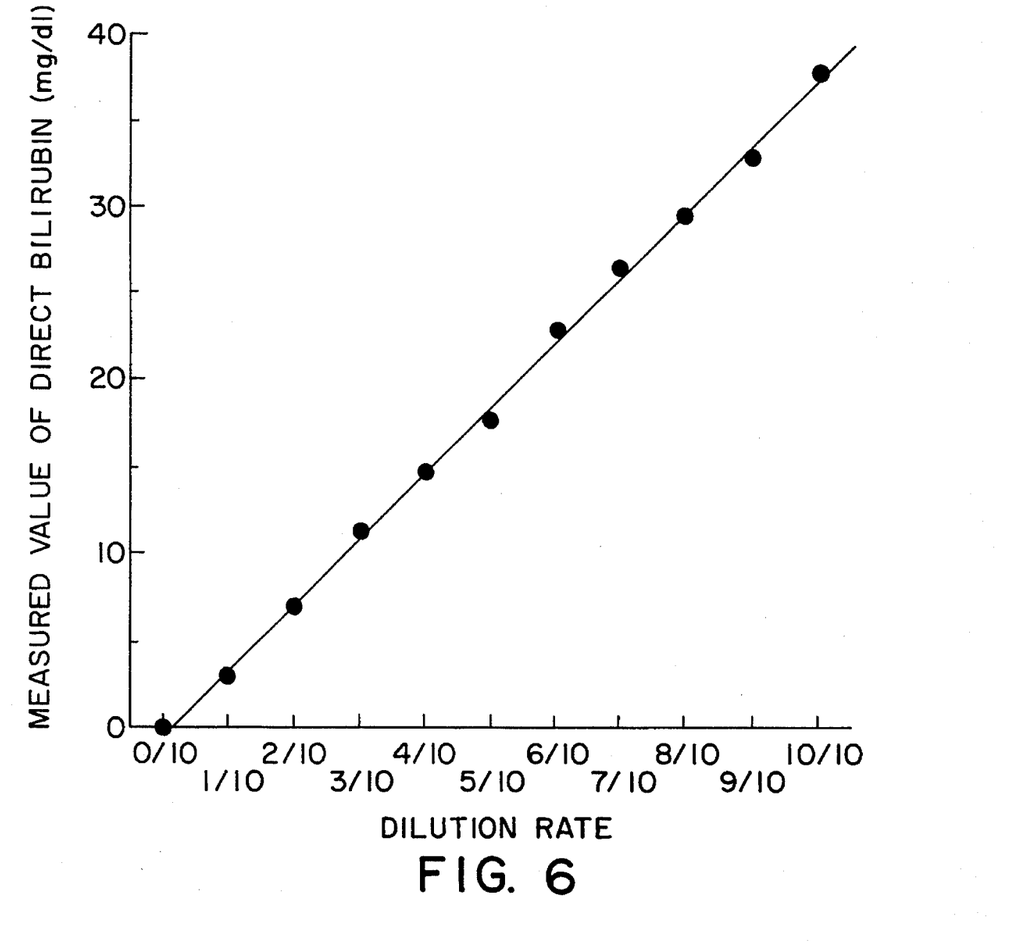
FIG. 6 shows the relation between the measured value of direct bilirubin and the dilution rate of samples wherein the samples are the direct bilirubin by the reagent of the present invention using enzymes derived from Myrothecium as bilirubin oxidase.

Reagents 3, 4 and 10 were used in place of reagents 1, 2 and 9, respectively, as example 1 and comparative example 1 to measure the direct bilirubin in the same procedures. The result is shown in FIG. 1 (example 2 and comparative example 2). Reagents 5, 6 and 11 (example 3 and comparative example 3), and reagents 7, 8 and 12 (example 4 and comparative example 4) were used in place of reagents 1, 2 and 9, respectively, to measure the direct bilirubin in the same procedures as example 1 and comparative example 1. The result is shown in FIG. 2.

The above results show that the indirect bilirubin is not oxidized by the reagents of the present invention.

Working Example 5 to 8

Measurements were taken in the same manner as in examples 1 to 4 except that the direct bilirubin specimen (specimen 5) was used in place of the indirect bilirubin specimen (specimen 1). The relation between measured values and the dilution rate of specimens is shown in FIG. 3 to 6 (example 5 to 8). The relation between them is represented by a straight line passing through a point close to the origin, indicating that the reagent using bilirubin oxidase of the present invention has a sufficient range of measurement to be used in the clinical examination.

Example 9 to 12

Comparative Example 5

Specimen 2, 3 or 4 (0.01 ml) was added to reagent 13 (0.28 ml). The mixture was heated at 37 degC for 5 minutes. Absorbance of the mixture was measured at 450 nm (subwave-length 546 nm) by correcting the sample blank for the final volume by assuming the addition of reagent 2. Then reagent 18 (0.07 ml) was added to the mixture. The mixture was allowed to react at 37 degC for 5 minutes. Then absorbance was measured at 450 nm (subwavelength 546 nm). The amount the direct bilirubin in the specimen was determined using ditaurobilirubin of a known concentration as the standard. The result is shown in Table 1 (comparative example 5). Measurements were similarly taken using reagents 14 to 17 in place of reagent 13 in comparative example 5. The result (example 9 to 12) is shown in Table 1 together with the result of comparative example 5.

The above results show that the indirect bilirubin is not oxidized by the reagent using an oxidizing agent of the present invention.

TABLE 1

|  | Specimen 1 | Specimen 2 | Specimen 3 |
| --- | --- | --- | --- |
| Comparative example 5 | 0.36 | 0.53 | 0.70 |
| Working example 9 | 0.38 | 0.43 | 0.48 |
| Working example 10 | 0.34 | 0.35 | 0.37 |
| Working example 11 | 0.13 | 0.18 | 0.15 |
| Working example 12 | 0.06 | 0.03 | 0.04 |

(mg/dl)

Example 13 to 16

Comparative Example 6

Specimen 2, 3 or 4 (0.01 ml) was added to reagent 19 (0.3 ml). The mixture was heated at 37 degC for 5 minutes. Absorbance of the mixture was measured at 546 nm (subwave-length 660 nm) by correcting the sample blank for the final volume by assuming the addition of reagent 2. Then reagent 24 (0.15 ml) was added to the mixture. The mixture was allowed to react at 37 degC for 5 minutes. Then absorbance was measured at 546 nm (subwavelength 660 nm). The amount of the direct bilirubin in the specimen was determined using ditaurobilirubin of a known concentration as the standard. The result is shown in Table 2 (comparative example 6). Measurements were similarly taken using reagents 20 to 23 in place of reagent 19 in comparative example 6. The result (examples 13 to 16) is shown in Table 2 together with the result of comparative example 6.

The above results show that the indirect bilirubin is not oxidized by the reagent using a diazonium salt of the present invention.

TABLE 2

|  | Specimen 1 | Specimen 2 | Specimen 3 |
|---|---|---|---|
| Comparative example 6 | 0.32 | 0.55 | 0.78 |
| Working example 13 | 0.34 | 0.45 | 0.52 |
| Working example 14 | 0.45 | 0.41 | 0.45 |
| Working example 15 | 0.39 | 0.37 | 0.35 |
| Working example 16 | 0.40 | 0.41 | 0.41 |

(mg/dl)

Example 17 to 20

Comparative Example 7

Specimen 2, 3 or 4 (0.01 ml) was added to reagent 25 (0.15 ml). The mixture was heated at 37 degC for 5 minutes. Reagent 30 (0.3 ml) was added and the mixture was further heated at 37 degC for 5 minutes for reaction. Absorbance of this reaction solution was measured at 600 nm (subwavelength 660 nm). The amount of the direct bilirubin in the specimen was determined using ditaurobilirubin of a known concentration as the standard. The result is shown in Table 3 (comparative example 7). Measurements were similarly taken using reagents 26 to 29 in place of reagent 25 in comparative example 7. The result (examples 17 to 20) is shown in Table 3 together with the result of comparative example 7.

The above results show that the indirect bilirubin is not oxidized by the reagent using a diagonium salt of the present invention, even when other measuring methods were used.

TABLE 3

|  | Specimen 2 | Specimen 3 | Specimen 4 |
|---|---|---|---|
| Comparative example 7 | 0.35 | 0.51 | 0.71 |
| Working example 17 | 0.27 | 0.38 | 0.49 |
| Working example 18 | 0.39 | 0.43 | 0.43 |
| Working example 19 | 0.31 | 0.32 | 0.35 |
| Working example 20 | 0.14 | 0.19 | 0.19 |

(mg/dl)

Example 21 to 32

Figure 7:
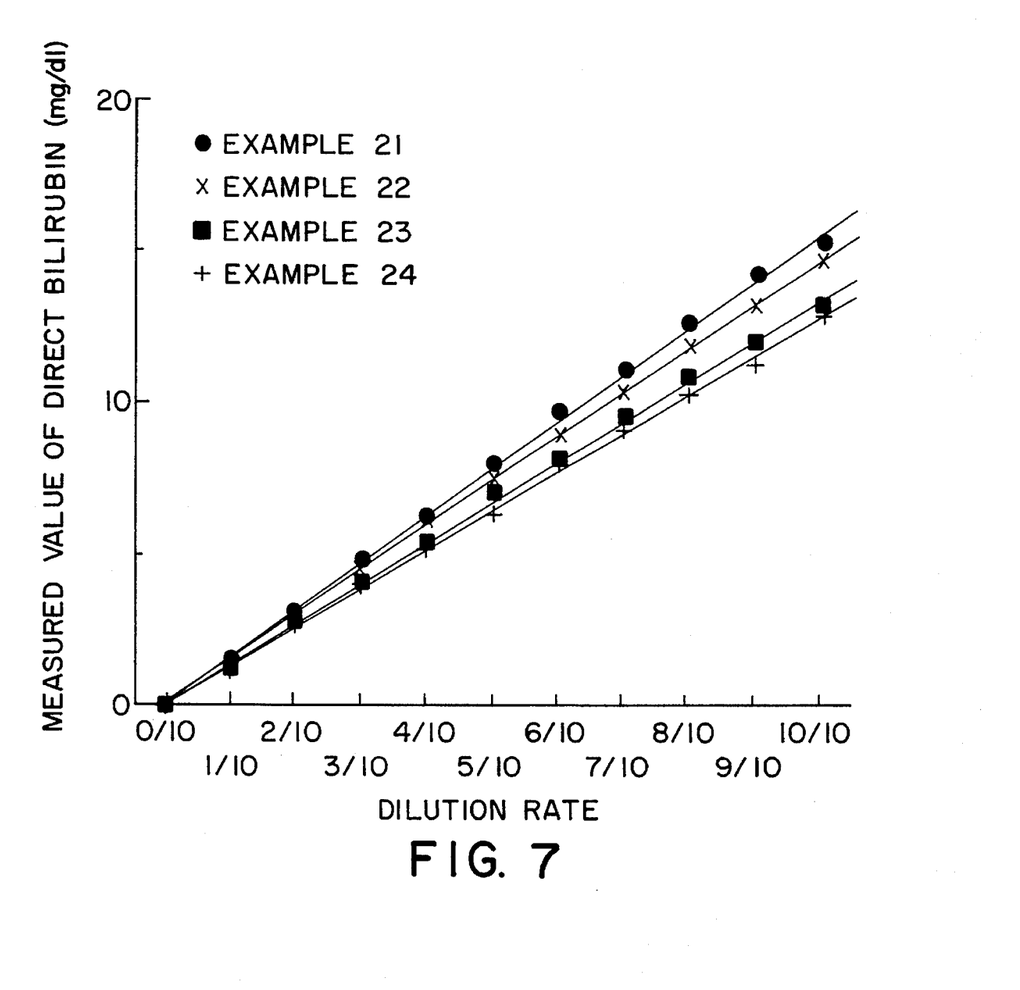
FIG. 7 shows the relation between the measured value of direct bilirubin and the dilution rate of samples wherein the samples are the direct bilirubin by the reagent (examples 21 to 24) of the present invention.
Figure 8:
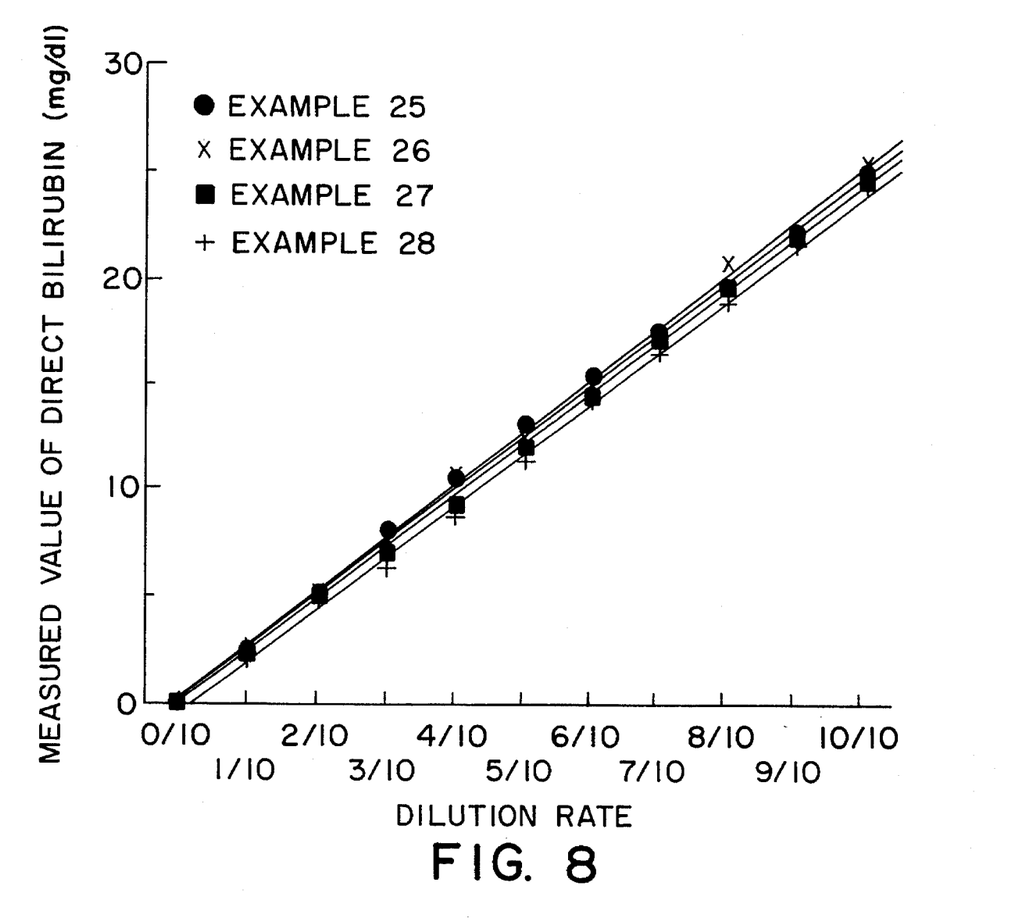
FIG. 8 shows the relation between the measured value of direct bilirubin and the dilution rate of samples wherein the samples are the direct bilirubin by the reagent (examples 25 to 28) of the present invention.
Figure 9:
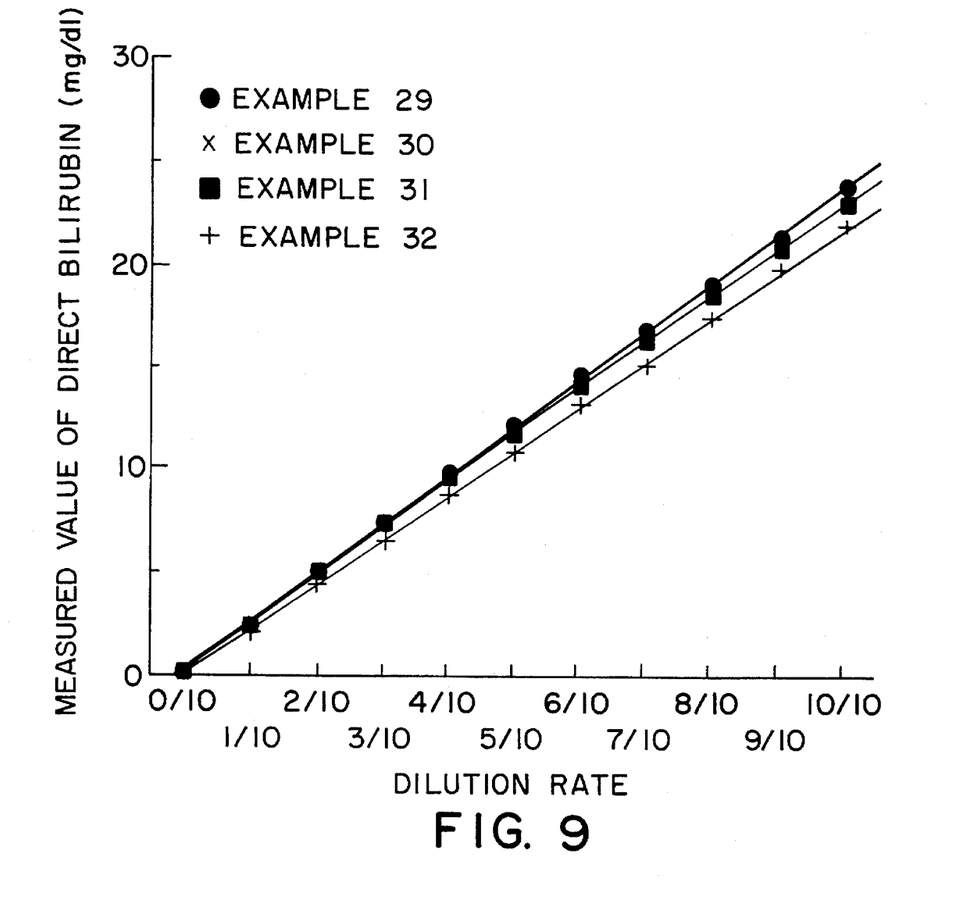
FIG. 9 shows the relation between the measured value of direct bilirubin and the dilution rate of samples wherein the samples are the direct bilirubin by the reagent (examples 29 to 32) of the present invention.

The same measurements were taken using the direct bilirubin specimen of specimen 5 in place of the indirect bilirubin specimen (specimen 1) in examples 9 to 12, examples 13 to 16, and example 17 to 20 (examples 21 to 24, examples 25 to 28, and example 29 to 32). The relation between measured values and the dilution rate of specimens is shown in FIG. 7 (example 21 to 24), FIG. 8 (example 25 to 28), and FIG. 9 (example 29 to 32). The relation between the measured values and the dilution rate of specimens is represented by a straight line passing through a point close to the origin, indicating that the reagent using an oxidizing agent or diazonium salt of the present invention has a sufficient range of the measurement to be used in the clinical examination, etc.

As described in detail in the above, the present invention allows accurate separation and measurement of the direct bilirubin, which is known to significantly increase in the biological fluids of patients of obstructive jaundice, etc., and is useful in clinical examination, etc.

What is claimed is:

1. A reagent system for measuring direct bilirubin in a specimen, which reagent system comprises a buffer, a tetrapyrrole compound, and a bilirubin-oxidizing compound selected from the group consisting of a bilirubin oxidase, an oxidizing agent, and a diazonium salt.

2. The reagent system of claim 1, wherein the tetrapyrrole compound is selected from the group consisting of bilirubin, biliverdin, urobilinogen, and combinations thereof.

3. The reagent system of claim 1, wherein the tetrapyrrole compound is present at a concentration of 0.01 to 100 µg/ml.

4. The reagent system of claim 3, wherein the tetrapyrrole compound is present at a concentration of 0.1 to 40 µg/ml.

5. A reagent system for measuring direct bilirubin in a specimen, which reagent system comprises a first component containing a buffer and a tetrapyrrole compound, and a second component containing a bilirubin-oxidizing compound selected from a bilirubin oxidase, an oxidizing agent, and a diazonium salt.

6. The reagent system of claim 5, wherein the tetrapyrrole compound is selected from the group consisting of bilirubin, biliverdin, urobilinogen, and combinations thereof.

7. The reagent system of claim 6, wherein the tetrapyrrole compound is present at a concentration of 0.01 to 100 µg/ml.

8. The reagent system of claim 7, wherein the tetrapyrrole compound is present at a concentration of 0.1 to 40 µg/ml.

9. A method for determining the concentration of direct bilirubin in a specimen comprising:

(a) combining the specimen with a buffer and a tetrapyrrole compound to form a first solution thereof;

(b) heating the first solution;

(c) measuring absorbance of the first solution at a specified wavelength;

(d) adding a bilirubin-oxidizing compound selected from a bilirubin oxidase, an oxidizing agent, and a diazonium salt to the first solution to form a second solution thereof;

(e) measuring absorbance of the second solution at the specified wavelength, and determining a change in absorbance (A) between the absorbance of the first and second solutions;

(f) performing steps (a)–(e) on a standard sample containing direct bilirubin at a known concentration to determine a change in absorbance (B) for the standard sample; and (g) relating A, B, and the known concentration of direct bilirubin in the standard sample to determine the concentration of direct bilirubin in the specimen.

* * * * *